United States Patent
Goble et al.

(10) Patent No.: US 6,942,662 B2
(45) Date of Patent: Sep. 13, 2005

(54) SURGICAL INSTRUMENT

(75) Inventors: Coliin C. O. Goble, Surrey (GB); Kester J. Batchelor, Gwent (GB); Mark G. Marshall, Berkshire (GB)

(73) Assignee: Gyrus Group PLC, Berkshire (GB)

( * ) Notice: Subject to any disclaimer, the term of this patent is extended or adjusted under 35 U.S.C. 154(b) by 122 days.

(21) Appl. No.: 10/324,069

(22) Filed: Dec. 20, 2002

(65) Prior Publication Data

US 2003/0130658 A1 Jul. 10, 2003

Related U.S. Application Data

(63) Continuation-in-part of application No. 10/105,811, filed on Mar. 21, 2002, now Pat. No. 6,832,998.

(30) Foreign Application Priority Data

| Dec. 27, 2001 | (GB) | 0130975 |
| Mar. 15, 2002 | (GB) | 0206207 |
| Jul. 3, 2002 | (GB) | 0215402 |

(51) Int. Cl.$^7$ .............................................. A61B 18/14
(52) U.S. Cl. ......................................... 606/48; 606/50
(58) Field of Search ................................ 606/45, 48–50

(56) References Cited

U.S. PATENT DOCUMENTS

| 3,970,088 A | 7/1976 | Morrison |
| 4,228,800 A | * 10/1980 | Degler et al. ............... 606/48 |
| 4,476,862 A | 10/1984 | Pao |
| 4,706,667 A | * 11/1987 | Roos ........................... 606/48 |
| 5,269,780 A | 12/1993 | Roos |
| 5,330,470 A | * 7/1994 | Hagen ......................... 606/48 |
| 5,423,807 A | 6/1995 | Milder |
| 5,895,386 A | 4/1999 | Odell et al. |
| 6,106,524 A | 8/2000 | Eggers et al. |
| 6,203,542 B1 | 3/2001 | Ellsberry et al. |
| 6,306,134 B1 | 10/2001 | Goble et al. |
| 6,322,549 B1 | 11/2001 | Eggers et al. |
| 2001/0014804 A1 | 8/2001 | Goble et al. |

FOREIGN PATENT DOCUMENTS

| EP | 0 453 071 A | 10/1991 |
| EP | 0 795 301 B1 | 9/1997 |
| EP | 0 795 301 A1 | 9/1997 |
| EP | 1 025 807 A2 | 8/2000 |
| EP | 1 080 680 A1 | 3/2001 |
| GB | 2 037 167 A | 7/1980 |
| GB | 2 053 686 A | 2/1981 |

* cited by examiner

Primary Examiner—Lee S. Cohen
(74) Attorney, Agent, or Firm—Nixon & Vanderhye, P.C.

(57) ABSTRACT

An electrosurgical cutting blade (1) comprises a first electrode (2), a second electrode (3), and an electrical insulator (4) separating the first and second electrodes. The first and second electrodes have dissimilar characteristics (cross-sectional area, thermal conductivity etc.) such that the first electrode (2) is encouraged to become an active electrode and the second electrode (3) is encouraged to become a return electrode. The spacing between the first and second electrodes (between 0.25 mm and 3.0 mm) and the peak voltage supplied to the electrodes (2 and 3) are both selected such that arcing does not occur directly between the electrodes, but between the first electrode and the tissue at the target site. The arrangement is such that, in use, a thermal differential of at least 50° C. is established between the first and second electrodes (2 and 3), such that the second electrode is maintained below a temperature of 70° C. This is achieved either by thermally insulating the second electrode from the first electrode, and/or by transferring heat away from the second electrode, e.g. by conduction, forced cooling, or by means of a heat pipe (27).

8 Claims, 7 Drawing Sheets

SURGICAL INSTRUMENT

This application is a continuation-in-part application of U.S. application Ser. No. 10/105,811, filed Mar. 21, 2002, now U.S. Pat. No. 6,823,998.

BACKGROUND OF THE INVENTION

1. Field of the Invention

This invention relates to a bipolar electrosurgical cutting device such as a scalpel blade, and to an electrosurgical system comprising an electrosurgical generator and a bipolar electrosurgical cutting device. Such systems are commonly used for the cutting of tissue in surgical intervention, most commonly in "keyhole" or minimally invasive surgery, but also in "open" surgery.

2. Description of Related Art

Electrosurgical cutting devices generally fall into two categories, monopolar and bipolar. In a monopolar device a radio frequency (RF) signal is supplied to an active electrode which is used to cut tissue at the target site, an electrical circuit being completed by a grounding pad which is generally a large area pad attached to the patient at a location remote from the target site. In contrast, in a bipolar arrangement both an active and a return electrode are present on the cutting device, and the current flows from the active electrode to the return electrode, often by way of an arc formed therebetween.

An early example of a bipolar RF cutting device is U.S. Pat. No. 4,706,667 issued to Roos, in which the return or "neutral" electrode is set back from the active electrode. Details for the areas of the cutting and neutral electrodes are given, and the neutral electrode is said to be perpendicularly spaced from the active electrode by between 5 and 15 mm. In a series of patents including U.S. Pat. No. 3,970,088, U.S. Pat. No. 3,987,795 and U.S. Pat. No. 4,043,342, Morrison describes a cutting/coagulation device which has "sesquipolar" electrode structures. These devices are said to be a cross between monopolar and bipolar devices, with return electrodes which are carried on the cutting instrument, but which are preferably between 3 and 50 times larger in area than the cutting electrode. In one example (U.S. Pat. No. 3,970,088) the active electrode is covered with a porous, electrically-insulating layer, separating the active electrode from the tissue to be treated and causing arcing between the electrode and the tissue. The insulating layer is said to be between 0.125 and 0.25 mm (0.005 and 0.01 inches) in thickness.

In another series of patents (including U.S. Pat. No. 4,674,498, U.S. Pat. No. 4,850,353, U.S. Pat. No. 4,862,890 and U.S. Pat. No. 4,958,539) Stasz proposed a variety of cutting blade designs. These were designed with relatively small gaps between two electrodes such that arcing would occur therebetween when an RF signal was applied to the blade, the arcing causing the cutting of the tissue. Because arcing was designed to occur between the electrodes, the typical thickness for the insulating material separating the electrodes was between 0.025 and 0.075 mm (0.001 and 0.003 inches).

BRIEF SUMMARY OF THE INVENTION

The present invention seeks to provide a bipolar cutting blade which is an improvement over the prior art. Accordingly, there is provided an electrosurgical system comprising a bipolar cutting blade, a handpiece to which the cutting blade is secured, and an electrosurgical generator for supplying a radio frequency voltage signal to the cutting blade, the cutting blade comprising first and second electrodes, and an electrical insulator spacing apart the electrodes, the spacing being between 0.25 mm and 3.0 mm, and the electrosurgical generator being adapted to supply a radio frequency voltage signal to the cutting blade which has a substantially constant peak voltage value, the relationship between the peak voltage value and the spacing between the electrodes being such that the electric field intensity between the electrodes is between 0.1 volts/$\mu$m and 2.0 volts/$\mu$m, the first electrode having a characteristic which is dissimilar from that of the second electrode such that the first electrode is encouraged to become an active electrode and the second electrode is encouraged to become a return electrode.

By the term "blade", there is herein meant to include all devices which are designed such that both the active cutting electrode and the return electrode are designed to enter the incision made by the instrument. It is not necessary that the cutting device is only capable of making an axial incision, and indeed it will be shown below that embodiments of the present invention are capable of removing tissue in a lateral direction.

The first important feature of the present invention is that the spacing between the electrodes and the electric field intensity therebetween is carefully controlled such that there is no direct arcing between the electrodes in the absence of tissue. For the purposes of this specification, the spacing between the electrodes is measured in terms of the shortest electrical path between the electrodes. Thus, even if electrodes are adjacent on to another such that the straight-line distance therebetween is less than 0.25 mm, if the insulator separating the electrodes is such that this straight line is not available as a conductive pathway, then the "spacing" between the electrodes is the shortest available conductive path between the electrodes. The electric field intensity between the electrodes is preferably between 0.15 volts/$\mu$m and 1.5 volts/$\mu$m, and typically between 0.2 volts/$\mu$m and 1.5 volts/$\mu$m. In one preferred arrangement, the spacing between the first and second electrodes is between 0.25 mm and 1.0 mm, and the electric field intensity between the electrodes is between 0.33 volts/$\mu$m and 1.1 volts/$\mu$m. Preferably, the electric field intensity is such that the peak voltage between the first and second electrodes is less than 750 volts. This ensures that the field intensity is sufficient for arcing to occur between the first electrode and the tissue, but not directly between the first and second electrodes.

However, even where direct arcing between the electrodes is prevented, there is still a potential problem if the two electrodes are similar in design. In a bipolar cutting device only one of the electrodes will assume a high potential to tissue (and become the "active" electrode), with the remaining electrode assuming virtually the same potential as the tissue (becoming the "return" electrode). Where the first and second electrodes are similar, which electrode becomes the active can be a matter of circumstance. If the device is activated before becoming in contact with tissue, the electrode first contacting tissue will usually become the return electrode, with the other electrode becoming the active electrode. This means that in some circumstances one electrode will be the active electrode, and at other times the other electrode will be the active electrode. Not only does this make the device difficult for the surgeon to control (as it will be uncertain as to exactly where the cutting action will occur), but as it is likely that any particular electrode will at some time have been active.

When an electrode is active, there is a build up of condensation products on the surface thereof. This is not a problem when the electrode continues to be the active electrode, but it does make the electrode unsuitable for use as a return electrode. Thus, in the instance where two similar electrodes are employed, it is likely that, as each will at some times become active and at other times the return, the build up of products on both electrodes will lead to a decrease in performance of the instrument. Therefore, the present invention provides that the first electrode has a characteristic which is dissimilar from that of the second electrode, in order to encourage one electrode to assume preferentially the role of the active electrode.

The characteristic of the first electrode which is dissimilar from that of the second electrode conveniently comprises the cross-sectional area of the electrode, the cross-sectional area of the first electrode being substantially smaller than that of the second electrode. This will help to ensure that the first electrode (being of a smaller cross-sectional area) will experience a relatively high initial impedance on contact with tissue, while the relatively larger area second electrode will experience a relatively lower initial impedance on contact with tissue. This arrangement will assist in encouraging the first electrode to become the active and the second electrode to become the return.

The characteristic of the first electrode which is dissimilar from that of the second electrode alternatively or additionally comprises the thermal conductivity of the electrode, the thermal conductivity of the first electrode being substantially lower than that of the second electrode. In addition to the initial impedance, the rate of rise of the impedance is a factor influencing which electrode will become active. The impedance will rise with desiccation of the tissue, and the rate of desiccation will be influenced by the temperature of the electrode. By selecting an electrode material with a relatively low thermal conductivity, the electrode temperature will rise quickly as little heat is conducted away from the part of the electrode at which energy is delivered. This will ensure a relatively fast desiccation rate, producing a correspondingly fast rise in impedance and ensuring that the first electrode remains the active electrode.

The characteristic of the first electrode which is dissimilar from that of the second electrode may further comprise the thermal capacity of the electrode, the thermal capacity of the first electrode being substantially lower than that of the second electrode. As before, a low thermal capacity helps to maintain the temperature of the first electrode at a relatively high level, ensuring that it remains the active electrode.

According to a further aspect of the invention, there is provided an electrosurgical system comprising a bipolar cutting blade, a handpiece to which the cutting blade is secured, and an electrosurgical generator for supplying a radio frequency voltage signal to the cutting blade, the cutting blade comprising first and second electrodes, and an electrical insulator spacing apart the electrodes, the spacing being between 0.25 mm and 1.0 mm, and the electrosurgical generator being adapted to supply a radio frequency voltage signal to the cutting blade which has a substantially constant peak voltage value, the peak voltage value being respectively between 250 volts and 600 volts, the first electrode having a characteristic which is dissimilar from that of the second electrode such that the first electrode is encouraged to become an active electrode and the second electrode is encouraged to become a return electrode.

Given a particular electrode separation, it is highly desirable that the generator delivers the same peak voltages despite varying load conditions. Heavy loading of the blade may otherwise make it stall (as load impedance approaches source impedance, the voltage may otherwise halve), while light loading may otherwise result in voltage overshoots and direct arcing between the electrodes.

The invention also resides in a bipolar cutting blade comprising first and second electrodes and an electrical insulator spacing apart the electrodes, the first electrode having a characteristic which is dissimilar from that of the second electrode such that the first electrode is encouraged to become an active electrode and the second electrode is encouraged to become a return electrode, the spacing between the electrodes being between 0.25 mm and 1.0 mm, such that when the electrodes are in contact with tissue and an electrosurgical cutting voltage is applied therebetween, arcing does not occur directly between the electrodes, there also being provided means for ensuring that the temperature of the second electrode does not rise above 70° C.

As well as ensuring that the second electrode does not become active, it is also important to ensure that the temperature of the second electrode does not rise above 70° C., the temperature at which tissue will start to stick to the electrode. The means for ensuring that the temperature of the second electrode does not rise above 70° C. conveniently comprises means for minimising the transfer of heat from the first electrode to the second electrode. One way of achieving this is to ensure that the first electrode is formed from a material having a relatively poor thermal conductivity, preferably less than 20 W/m.K. By making the first electrode a poor thermal conductor, heat is not transferred effectively away from the active site of the electrode and across to the second electrode, thereby helping to prevent the temperature of the second electrode from rising.

Alternatively or additionally, the heat can be inhibited from transferring from the first electrode to the second electrode by making the electrical insulator separating the electrodes from a material having a relatively poor thermal conductivity, preferably less than 40 W/m.K. Again, this helps to prevent heat generated at the first electrode from transferring to the second electrode.

Another way of inhibiting the transfer of heat is to attach the first electrode to the electrical insulator in a discontinuous manner. Preferably, the first electrode is attached to the electrical insulator at one or more point contact locations, and/or is perforated with a plurality of holes such as to reduce the percentage contact with the electrical insulator.

A preferred material for the first electrode is tantalum. When tantalum is used for the active electrode, it quickly becomes coated with a layer of oxide material. This tantalum oxide is a poor electrical conductor, helping to ensure that the first electrode maintains its high impedance with respect to the tissue, and remains the active electrode.

Another way of helping to ensure that the temperature of the second electrode does not rise above 70° C. is to maximise the transfer of heat away from the second electrode. Thus any heat reaching the second electrode from the first electrode is quickly transferred away before the temperature of the second electrode rises inordinately. One way of achieving this is to form the second electrode from a material having a relatively high thermal conductivity, preferably greater than 150 W/m.K.

The second electrode may conveniently be provided with additional cooling means to remove heat therefrom, such as a heat pipe attached to the second electrode, or a cooling fluid constrained to flow along a pathway in contact with the second electrode. Whichever method is employed, it is advisable for there to be a temperature differential, in use, between the first and second electrodes of at least 50° C., and preferably of between 100 and 200° C.

Preferably, there is additionally provided a third electrode adapted to coagulate tissue. This coagulation electrode is conveniently attached to the second electrode with a further electrical insulator therebetween. It is necessary to ensure that the temperature of the coagulation electrode does not rise to too high a level, and so if the coagulation electrode is attached to the second electrode (which is designed in accordance with the present teaching to be a good thermal conductor), it is preferable to arrange that heat is easily transferred across the further electrical insulator. This can be achieved by making the further insulator from a material having a relatively high thermal conductivity, or more typically, if the further insulator is not a good thermal conductor, by ensuring that the further insulator is relatively thin, typically no more than around 50 µm. In this way the transfer of heat across the further electrical insulator is greater than 5 mW/mm$^2$.K.

In one arrangement, the second and third electrodes are formed as conductive electrodes on an insulating substrate. Thus both the second and third electrodes act as return electrodes when the blade is used to cut tissue with the first electrode. When the blade is used to coagulate tissue, a coagulating RF signal is applied between the second and third electrodes.

According to a further aspect of the invention, there is provided a bipolar cutting blade comprising first and second electrodes and an electrical insulator spacing apart the electrodes, the first electrode having a characteristic which is dissimilar from that of the second electrode such that the first electrode is encouraged to become an active electrode and the second electrode is encouraged to become a return electrode, the spacing between the electrodes being between 0.25 mm and 1.0 mm, such that when the electrodes are in contact with tissue and an electrosurgical cutting voltage is applied therebetween, arcing does not occur directly between the electrodes, there being additionally provided a third electrode adapted to coagulate tissue, the third electrode being separated from the second electrode by an additional insulator.

The second and third electrodes are conveniently provided in a side-by-side arrangement with the additional insulator therebetween. Alternatively, the second and third electrodes are provided as layers in a sandwich structure with the additional insulator therebetween. In one convenient arrangement the first, second and third electrodes are each provided as layers in a sandwich structure with layers of insulator therebetween.

In one arrangement a first one of the second and third electrodes is provided with a cut-out portion, and the other one of the second or third electrodes is provided with a protruding portion. Preferably, the cut-out portion of the one electrode accommodates the protruding portion of the other electrode, typically such that the protruding portion is flush with the electrode surrounding the cut-out portion.

Alternatively, the first, second and third electrodes are provided as layers in a sandwich structure with the first electrode being in the middle, there being layers of insulator between each of the electrodes. In one arrangement, the second and third electrodes are substantially semi-circular in cross-section, and the first electrode protrudes slightly beyond the periphery of the second and third electrodes.

According to a final aspect of the invention, there is provided a method of cutting tissue at a target site comprising providing a bipolar cutting blade comprising first and second electrodes and an electrical insulator spacing apart the electrodes, the first electrode having a characteristic which is dissimilar from that of the second electrode such that the first electrode is encouraged to become an active electrode and the second electrode is encouraged to become a return electrode; bringing the blade into position with respect to the target site such that the second electrode is in contact with tissue at the target site and the first electrode is adjacent thereto; supplying an electrosurgical cutting voltage to the cutting blade, the electrosurgical voltage and the spacing between the first and second electrodes being such that arcing does not occur in air between the first and second electrodes, but that arcing does occur between the first electrode and the tissue at the target site, current flowing through the tissue to the second electrode; and preventing heat build up at the second electrode such that the temperature of the second electrode does not rise above 70° C. Preferably, the method is such that both the first and second electrodes come into contact with tissue at the target site substantially simultaneously.

BRIEF DESCRIPTION OF THE SEVERAL VIEWS OF THE DRAWINGS

The invention will now be described by way of example only, with reference to the accompanying drawings, in which.

DETAILED DESCRIPTION OF THE INVENTION

Figure 1:
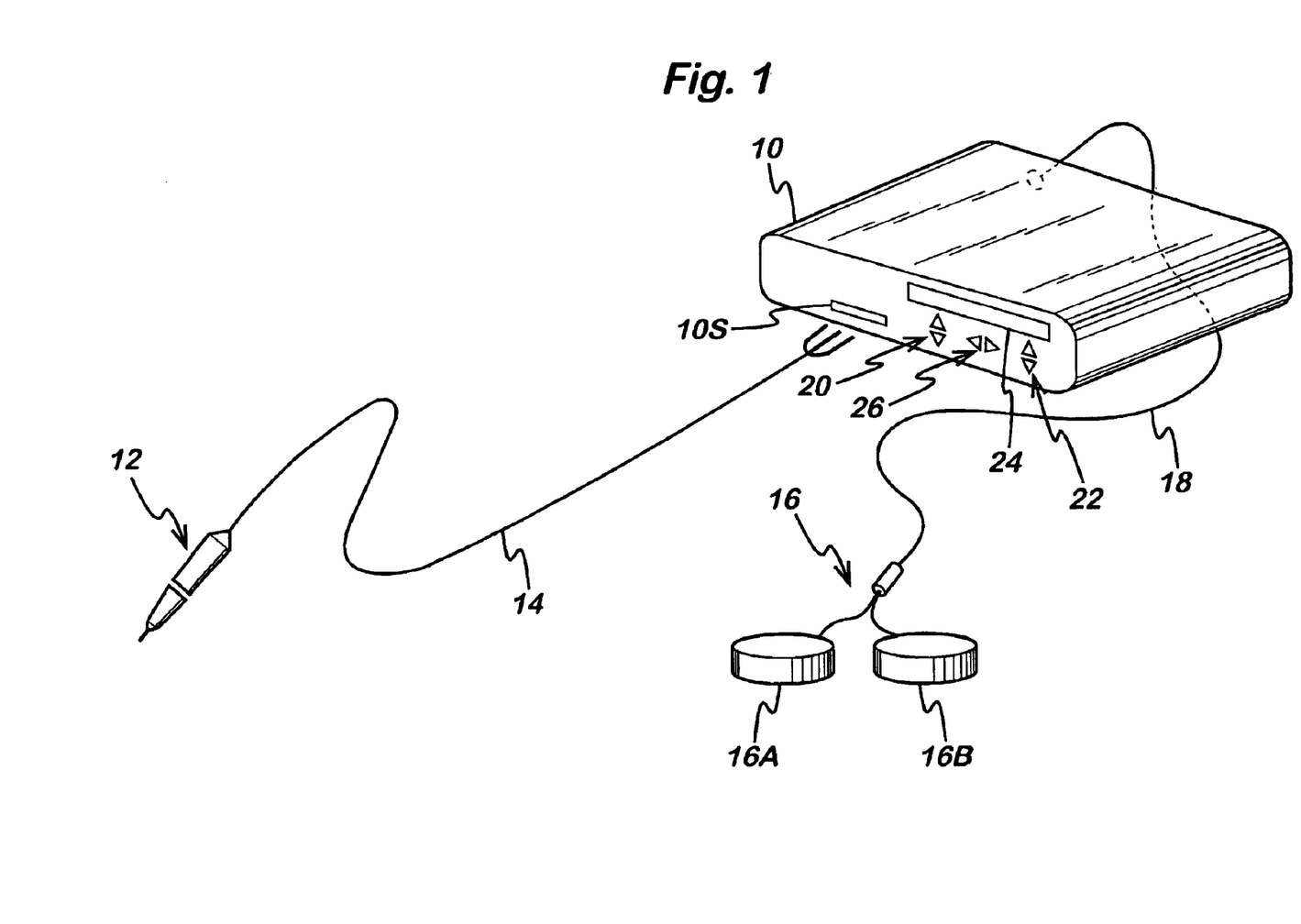
FIG. 1 is a schematic diagram of an electrosurgical system constructed in accordance with the present invention.

Referring to FIG. 1, a generator 10 has an output socket 10S providing a radio frequency (RF) output for an instrument 12 via a connection cord 14. Activation of the generator 10 may be performed from the instrument 12 via a connection in the cord 14, or by means of a footswitch unit 16, as shown, connected to the rear of the generator by a footswitch connection cord 18. In the illustrated embodiment, the footswitch unit 16 has two footswitches 16A and 16B for selecting a coagulation mode and a cutting mode of the generator 10 respectively. The generator front panel has push buttons 20 and 22 for respectively setting coagulation and cutting power levels, which are indicated in a display 24. Push buttons 26 are provided as an alternative means for selection between coagulation and cutting modes.

Figure 2:
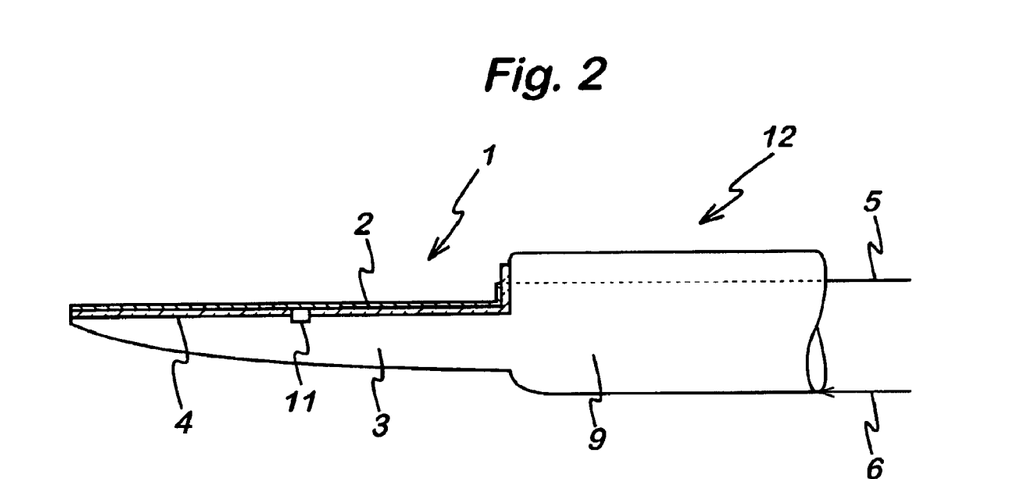
FIG. 2 is a schematic cross-sectional view of an electrosurgical cutting blade constructed in accordance with the present invention.

Referring to FIG. 2, the instrument 12 comprises a blade shown generally at 1 and including a generally flat first electrode 2, a larger second electrode 3, and an electrical insulator 4 separating the first and second electrodes. The first electrode 2 is formed of stainless steel having a thermal conductivity of 18 W/m.K (although alternative materials such as Nichrome alloy may also be used). The second electrode 3 is formed from a highly thermally-conducting material such as copper having a thermal conductivity of 400 W/m.K (alternative materials including silver or aluminium). The surface of the second electrode 3 is plated with a biocompatible material such as a chromium alloy, or with an alternative non-oxidising material such as nickel, gold, platinum, palladium, stainless steel, titanium nitride or tungsten disulphide. The electrical insulator 4 is formed from a ceramic material such as $Al_2O_3$ which typically has a thermal conductivity of 30 W/m.K. Other possible materials for the insulator 4 are available which have a substantially lower thermal conductivity. These include boron nitride, porcelain, steatite, Zirconia, PTFE, reinforced mica, silicon rubber or other ceramic materials such as foamed ceramics or mouldable glass ceramic such as that sold under the trademark MACOR.

Figure 3:
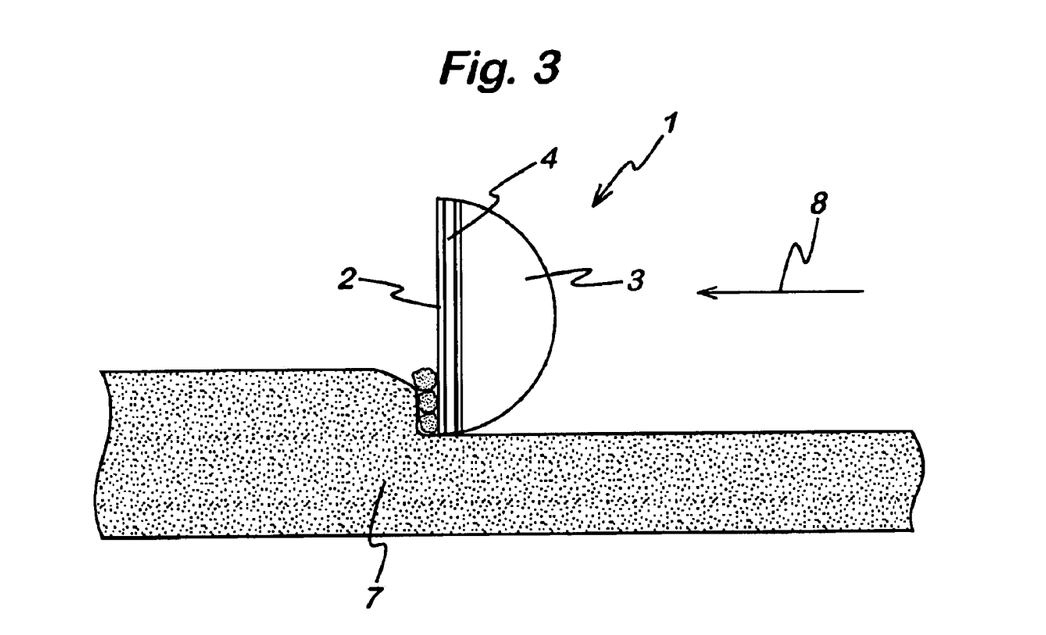
FIG. 3 is a schematic diagram showing the lateral cutting action of the blade of FIG. 2, FIGS. 4a to 4d are schematic cross-sectional views of alternative embodiments of electrosurgical cutting blades constructed in accordance with the invention.

A conductive lead 5 is connected to the first electrode 2, and a lead 6 is connected to the second electrode 3. The RF output from the generator 10 is connected to the blade 1 via the leads 5 and 6 so that a radio frequency signal having a substantially constant peak voltage (typically around 400V) appears between the first and second electrodes 2 and 3. Referring to FIG. 3, when the blade 1 is brought into contact with tissue 7 at a target site, the RF voltage will cause arcing between one of the electrodes and the tissue surface. Because the first electrode 2 is smaller in cross-sectional area, and has a lower thermal capacity and conductivity than that of the second electrode 3, the first electrode will assume the role of the active electrode and arcing will occur from this electrode to the tissue 7. Electrical current will flow through the tissue 7 to the second electrode 3, which will assume the role of the return electrode. Cutting of the tissue will occur at the active electrode, and the blade may be moved through the tissue. The blade 1 may be used to make an incision in the tissue 7, or moved laterally in the direction of the arrow 8 in FIG. 3 to remove a layer of tissue.

During cutting, considerable heat will be generated at the active electrode 2, and the electrode temperature may rise to 100–250° C. However, due to the poor thermal conductivity of the insulator 4, less heat is transmitted to the second electrode 3. Even when heat does reach the second electrode 3, the high thermal conductivity of the copper material means that much of the heat is conducted away from the electrode surface and into the body 9 of the electrode. This helps to ensure that a temperature differential is maintained between the first electrode 2 and the second electrode 3, and that the temperature of the second electrode 3 remains below 70° C. for as long as possible. This ensures that the second electrode 3 remains the return electrode whenever the instrument 12 is activated, and also that tissue does not begin to stick to the electrode 3.

Figure 4A:
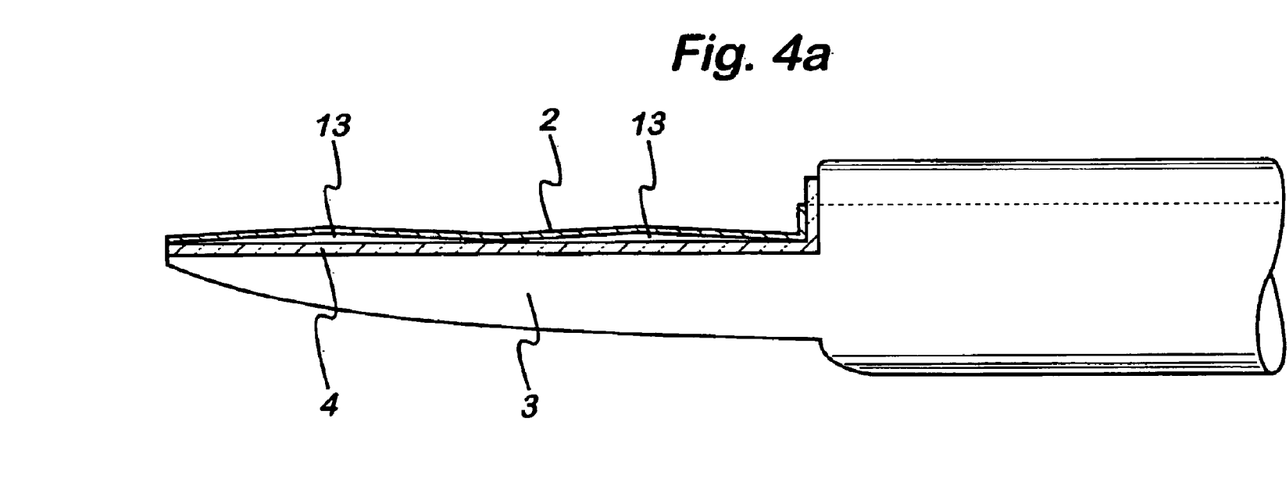
Figure 4B:
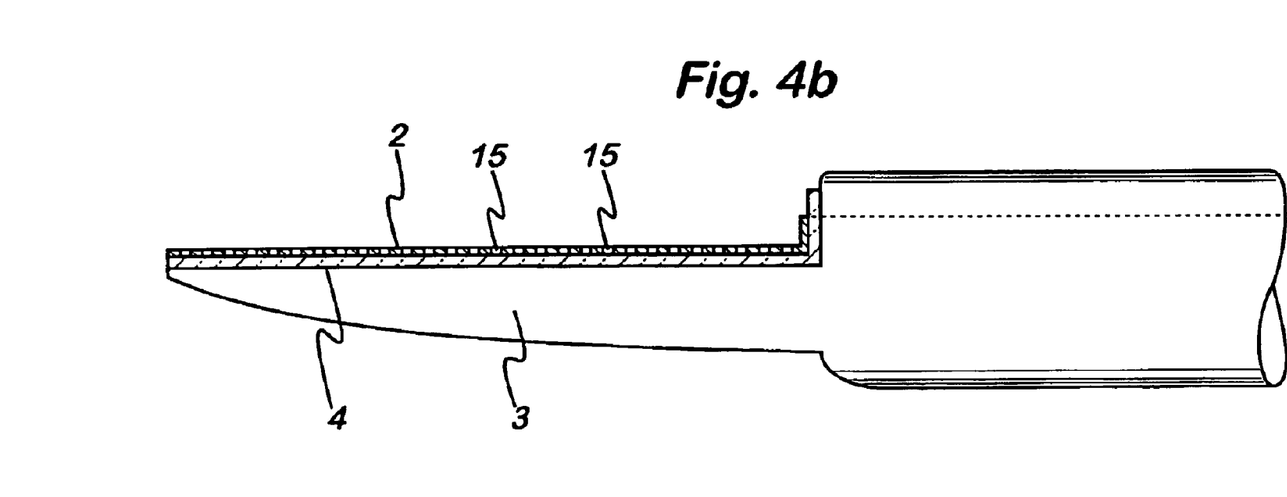
Figures 4C, 4D:
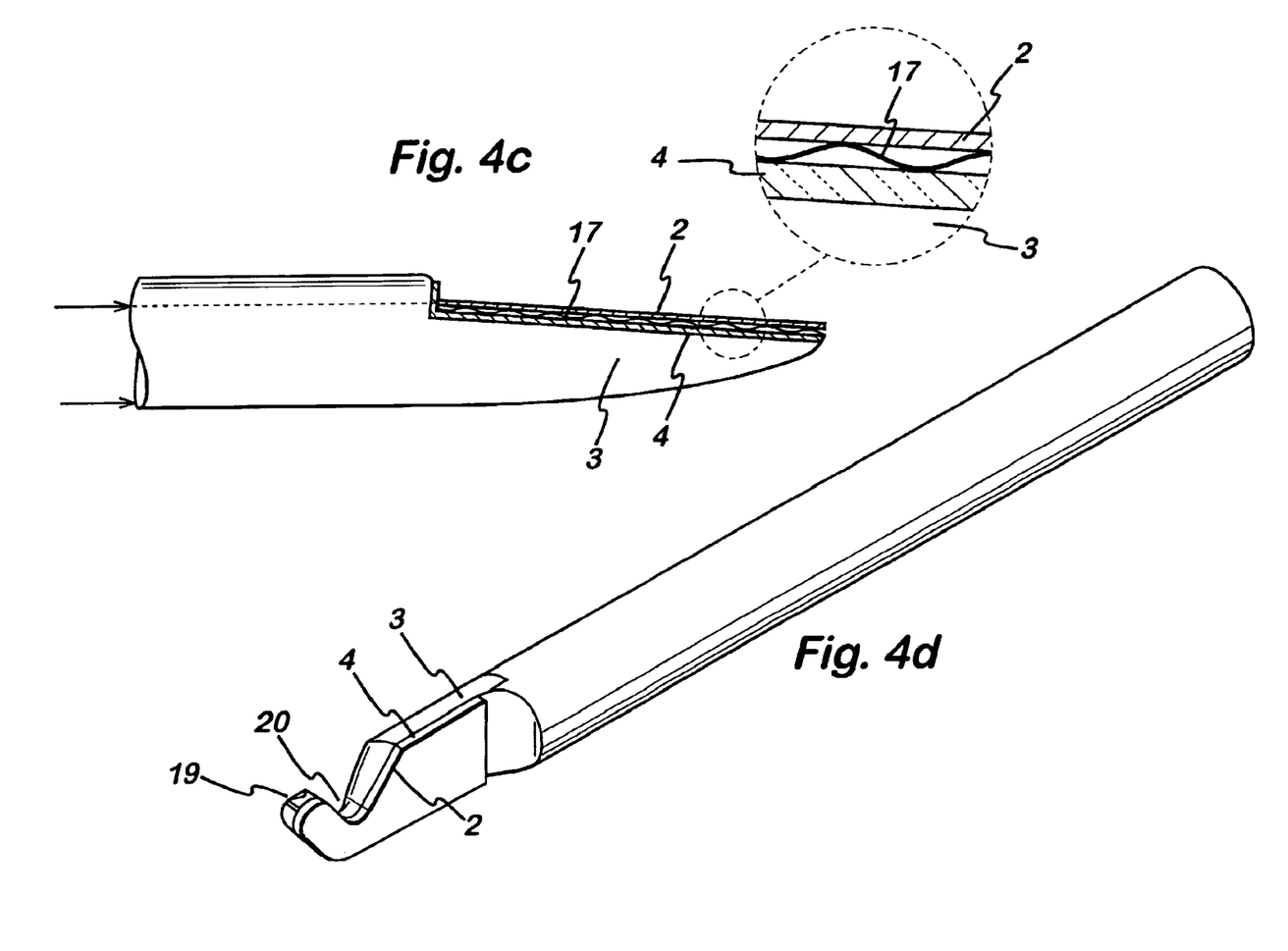

In addition to providing an insulator 4 which has a relatively low thermal conductivity, it is advantageous to ensure that the first electrode 2 contacts the insulator 4 as little as possible. In FIG. 2 the electrode 2 is not secured to the insulator 4 and the electrode 3 in a continuous fashion, but by one or more point contact pins shown generally at 11. FIG. 4*a* shows a further design of blade in which the first electrode 2 is shaped so as to contact the insulator 4 only intermittently along its length, with regions 13 over which the electrode bows outwardly from the insulator 4. This helps to minimise further the transfer of heat from the first electrode 2, through the insulator 4, to the second electrode 3. FIG. 4*b* shows a further arrangement in which the first electrode 2 is provided with many perforations 15 such that it is in the form of a mesh. Once again, this helps to minimise the transfer of heat from the first electrode 2 to the insulator 4. FIG. 4*c* shows another arrangement in which there is an additional corrugated electrode layer 17 located between the first electrode 2 and the insulator 4. As before, this assists in helping to prevent heat, generated at the first electrode 2 from reaching the second electrode 3, so as to maintain the thermal differential therebetween.

FIG. 4*d* shows a variation on the blade of FIG. 2, in which the blade is formed as a hook 19. The first electrode 2, the second electrode 3 and the insulator 4 are all hook-shaped, and the operation of the device is substantially as described with reference to FIG. 2. The hook electrode is particularly suited for parting tissue, whether used as a cold resection instrument without RF energisation, or as an RF cutting instrument. Tissue may be held in the angle 20 of the hook 19, while being manipulated or cut.

Figure 5A:
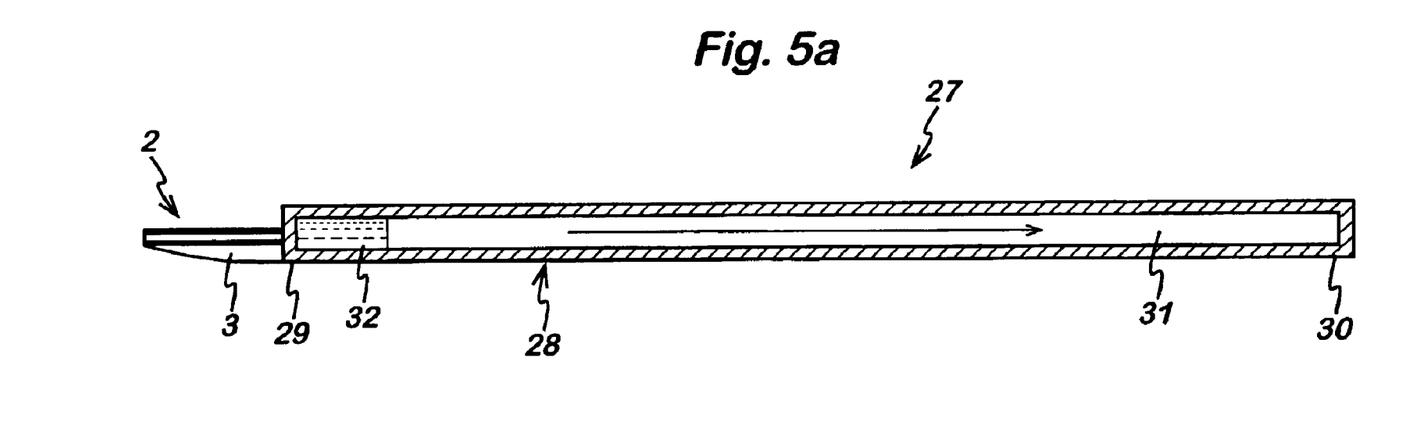
FIGS. 5a and 5b are schematic diagrams of electrosurgical cutting blades constructed in accordance with the present invention, incorporating cooling means.
Figure 5B:
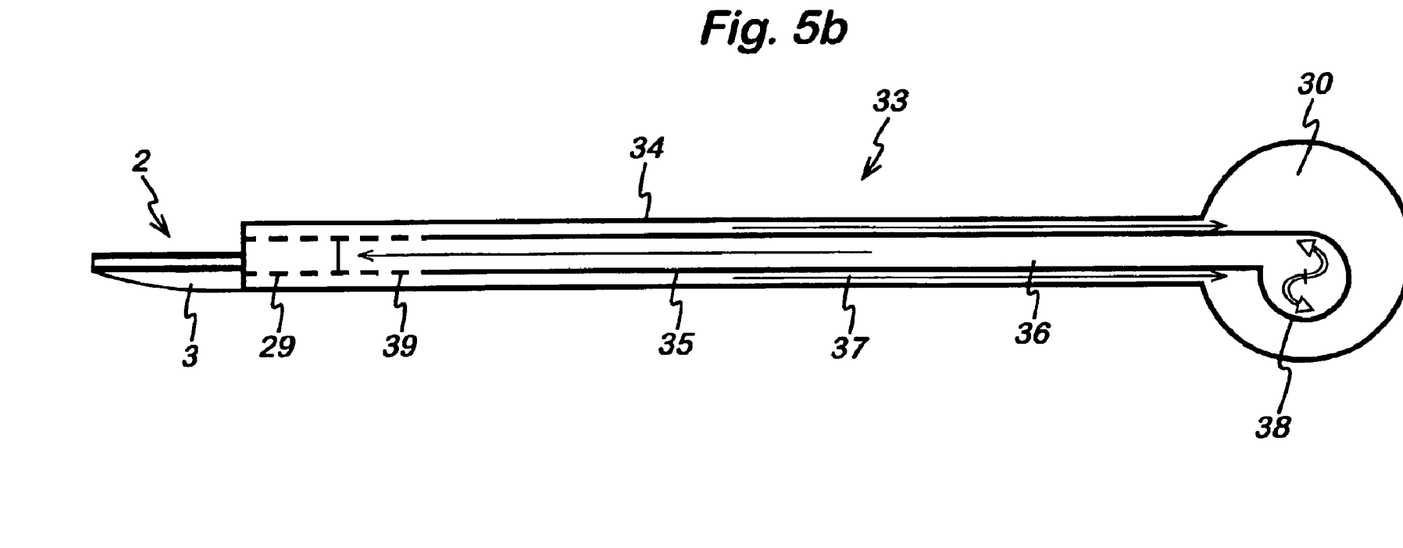

Whichever design of electrode is employed, it is advantageous if heat which does cross from the first electrode 2 to the second electrode 3 can be transferred away from the tissue contact surface of the electrode 3. In the blade of FIG. 2, the second electrode 3 is constituted by a relatively large mass of copper which is capable of conducting heat away from the electrode tip. The function of the electrode 3 can be further enhanced by employing cooling means as illustrated in FIGS. 5*a* and 5*b*. In FIG. 5*a*, the second electrode 3 is attached to a heat pipe shown generally at 27. The heat pipe 27 comprises a hollow closed tube 28 with a distal end 29 adjacent to the electrode 3, and a proximal end 30 within the handpiece of the instrument 12. The tube 28 has a cavity 31 therein, containing a low boiling temperature liquid 32 such as acetone or alcohol. In use, heat from the electrode 3 causes the liquid 32 at the distal end 29 of the tube to vaporise, and this vapour subsequently condenses at the proximal end 30 of the tube because it is relatively cool with respect to the distal end 29. In this way, heat is transferred from the distal end of the electrode 3 to the proximal end thereof, from where it can be further dissipated by the handpiece of the instrument 12.

FIG. 5*b* shows an alternative arrangement in which the heat pipe of FIG. 5*a* is replaced with a forced cooling system shown generally at 33. The cooling system 33 comprises a tube 34, again with a distal end 29 and a proximal end 30. The tube 34 includes a coaxial inner tube 35 defining an inner lumen 36 and an outer lumen 37. The inner tube 35 is perforated towards the distal end of the tube, so that the inner and outer lumens 36 and 37 are in communication one with another. In use, a self-contained pump 38 causes a cooling fluid 39 to be circulated up the inner lumen 36 to the distal end 29, returning via the outer lumen 37 to be recirculated continuously. The circulating fluid is heated by the electrode 3, and the heat is taken by the fluid to the proximal end 30 of the tube 34. In this way, the second electrode 3 is kept cool, despite the elevated temperature at the first electrode 2.

Figure 6A:
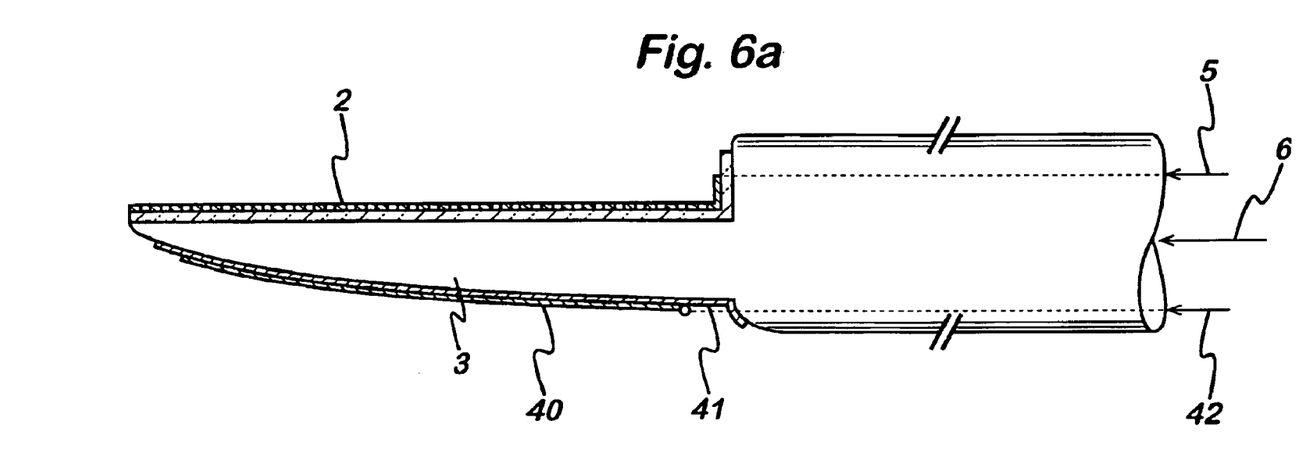
FIGS. 6a and 6b, and FIGS. 7 to 11 are alternative electrosurgical cutting blades constructed in accordance with the present invention, incorporating an additional coagulation electrode.

The remainder of the Figures show arrangements in which a third electrode 40 is provided, in order to allow the coagulation or desiccation of the tissue 7. In FIG. 6*a*, a blade 1 is shown in accordance with the construction of FIG. 4*b*, and like parts are designated with like reference numerals. The third electrode 40 is attached to the second electrode 3, on the opposite side to the first electrode 2, and mounted on a further electrical insulator 41. RF signals may be supplied to the third electrode 40 from the generator 10 via a lead 42. The insulator 41 is formed from a thin layer of silicon rubber, alternative materials for the insulator 41 including polyamide, PEEK or PVC materials. The thin layer ensures that heat can transfer across the silicon rubber layer and that the coagulation electrode 40 can benefit from the thermal conductivity properties of the second electrode 3. In this way, the coagulation electrode 40 can remain relatively cool despite any heat previously generated by the first electrode 2. In use, tissue is cut as previously described. When it is desired to coagulate instead of cutting, the third electrode 40 is placed in contact with the tissue 7, and a coagulating RF signal is applied between the second electrode 3 and the third electrode 40.

Figure 6B:
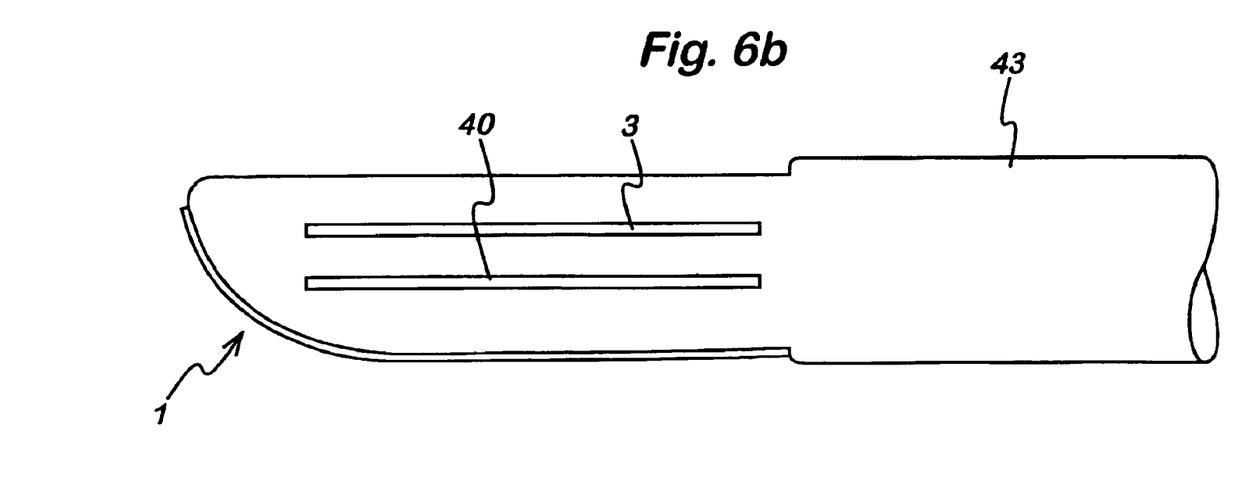

FIG. 6b shows an alternative embodiment in which the second electrode 3 and third electrode 40 are metallised tracks on a substrate 43 of aluminium nitride material. As before, this material is electrically insulating yet a good thermal conductor, to allow for the conduction of heat away from the second and third electrodes.

Figure 7:
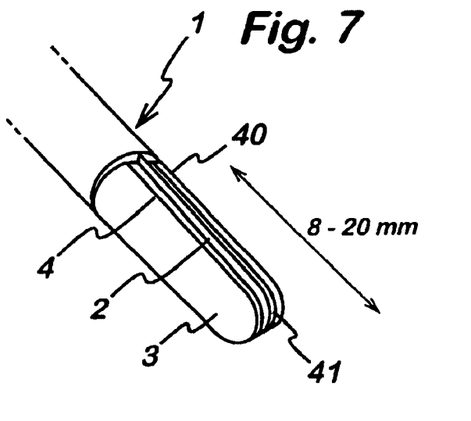

FIG. 7 shows an arrangement in which the first electrode 2 is located between the second and third electrodes 3 and 40. Both the electrodes 3 and 40 are approximately semi-circular in cross-section, and form a generally cylindrical structure with the first electrode 2 protruding slightly from the central region thereof. The insulating layer 4 separates the first electrode 2 from the second electrode 3, and the insulating layer 41 separates the first electrode 2 from the third electrode 40. When the user intends the instrument to cut tissue, the generator 10 applies a cutting RF signal between the first electrode 2 and one or both of the second or third electrodes 3, 40. Conversely, when the user intends the instrument to coagulate tissue, the generator 10 applies a coagulating RF signal between the second electrode 3 and the third electrode 40. The relatively large surface area of the electrodes 3 and 40 allows for effective coagulation of tissue, as well as for the conduction away of heat during cutting as previously described.

Figure 8:
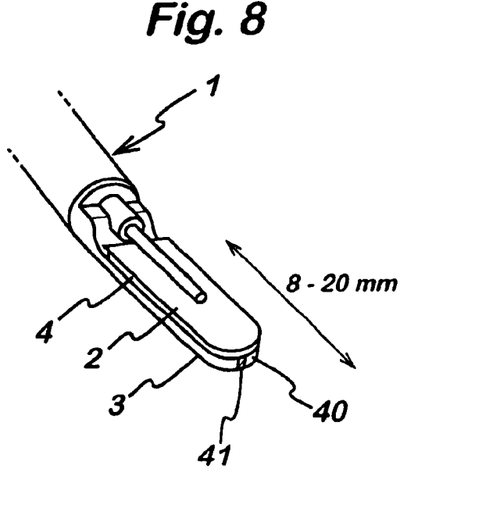

FIG. 8 shows an alternative design of instrument in which the second and third electrodes 3 and 40 are provided side-by-side. The first electrode 2 is substantially planar, and an insulating layer 4 separates the first electrode from the second and third electrodes 3 and 40 on the other side of the instrument. The electrodes 3 and 40 are disposed in side-by-side arrangement, with an insulating section 41 therebetween. As before, the instrument can cut tissue with an RF signal between the first electrode 2 and one of the second or third electrodes 3, 40, or alternatively coagulate tissue with an RF signal between the second and third electrodes.

Figure 9:
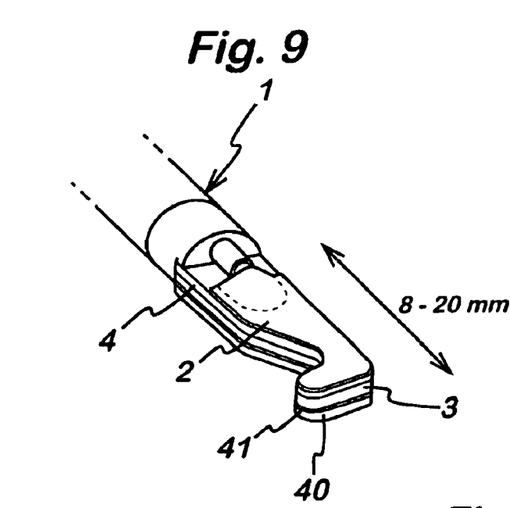

FIG. 9 shows a further embodiment in which the first, second and third electrodes are provided as a series of layers in a "sandwich" arrangement. The first electrode 2 is shown as the top layer in FIG. 9, with the third electrode 40 as the bottom layer, with the second electrode 3 sandwiched therebetween. Insulating layers 4 and 41 respectively serve to separate the first, second, and third electrodes. This arrangement provides a relatively thick edge to the blade 1, which is designed to facilitate coagulation of tissue.

Figure 10:
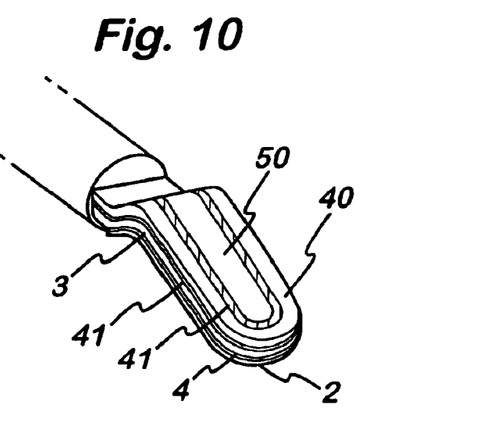

FIG. 10 shows an arrangement which utilises features from both the sandwich and side-by-side electrode structures. The electrodes are again provided in a sandwich arrangement, FIG. 10 showing the first electrode 2 on the bottom rather than the top as shown in FIG. 9. The second electrode 3 is again in the middle of the sandwich, separated from the first electrode by an insulating layer 4. The third electrode 40 is shown as the top electrode in FIG. 10, but has a central recess though which a raised portion 50 of the second electrode 3 can protrude. The second and third electrodes are separated by an insulator 41, and the top surface of the protrusion 50 is flush with the top of the third electrode 40. This arrangement allows either the sides of the blade 1 or the top face as shown in FIG. 10 to be used for the coagulation of tissue.

Figure 11:
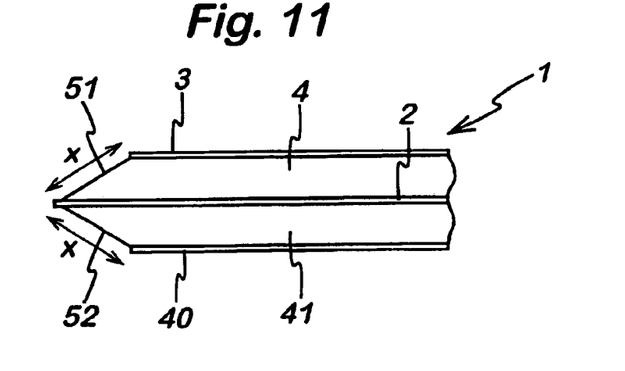

FIG. 11 shows an arrangement in which the end of the blade 1 comprises a central first electrode 2 with insulating layers 4 and 41 on either side thereof. The insulating layers 4 and 41 each have a slanting beveled distal end, as shown at 51 and 52 respectively. A second electrode 3 is attached to the insulating layer 4, the beveled end 51 resulting in the second electrode being set back axially from the first electrode 2 in the axis of the blade. In similar fashion, a third electrode 40 is attached to the insulating layer 41, the beveled end 52 resulting in the third electrode also being axially set back from the first electrode 2. The beveled ends 51 and 52 allow for a minimum separation (shown at "x" in FIG. 11) of 0.25 mm between the first electrode and the second and third electrodes, while maintaining an overall slim profile to the blade 1. The first electrode 2 can be flush with the ends of the first and second insulating layers 4 and 41, or may project slightly therefrom as shown in FIG. 11. As described previously, the transfer of heat by the first electrode can be reduced by a number of techniques, including attaching it to the insulating layers in a discontinuous manner, or perforating it with a plurality of holes in order to reduce heat transfer.

The invention relies on the careful selection of a number of design parameters, including the spacing between the first and second electrodes, the voltage supplied thereto, the size and materials selected for the electrodes, and for the electrical insulator or insulators. This careful selection should ensure that there is no direct arcing between the electrodes, that only one electrode is encouraged to be the active electrode, and that the return electrode is kept cool either by preventing heat reaching it and/or by transferring heat away from it should the heat reach the second electrode.

The relatively cool return electrode ensures that there is relatively little or no thermal damage to tissue adjacent the return of the instrument, while the tissue assists in the conduction of heat away from the return.

What is claimed is:

1. A bipolar cutting blade comprising:
    a first electrode,
    a second electrode,
    an electrical insulator spacing apart the first and second electrodes,
    the first electrode having a characteristic which is dissimilar from that of the second electrode, such that the first electrode is encouraged to become an active electrode and the second electrode is encouraged to become a return electrode,
    the spacing between the first and second electrodes being between 0.25 mm and 1.0 mm, such that when the first and second electrodes are in contact with tissue and an electrosurgical cutting voltage is applied therebetween, arcing does not occur directly between the first and second electrodes, and
    a third electrode adapted for coagulating tissue, the third electrode being separated from the second electrode by an additional insulator,
    wherein the firs electrode is substantially planar, and
    wherein the electrical insulator spaces apart the first electrode from the second and third electrodes on the other side of the bipolar cutting blade.

2. The bipolar cutting blade according to claim 1, wherein the second an third electrodes are provided in a side-by-side arrangement with the additional insulator therebetween.

3. The bipolar cutting blade according to claim 1, wherein the characteristic of the first electrode which is dissimilar from that of the second electrode cornprises the cross-sectional area of the electrode, the cross-sectional area of the first electrode being substantially smaller than that of the second electrode.

4. The bipolar cutting blade according to claim 1, wherein the characteristic of the first electrode which is dissimilar from that of the second electrode corn rises the thermal conductivity of the electrode, the thermal conductivity of the fir t electrode being substantially lower than that of the second electrode.

5. The bipolar cutting blade according to claim 1, wherein the characteristic of the first electrode which is dissimilar from that of the second electrode corn rises the thermal capacity of the electrode, the thermal capacity of the first electrode being substantially lower than that of the second electrode.

6. The bipolar cutting blade according to claim 1, wherein when the lade is used to cut tissue, the electrosurgical cutting voltage being applied between the first electrode and one of the second or third electrodes.

7. The bipolar cutting blade according to claim 1, wherein when the blade is used to coagulate tissue, the electrosurgical cutting voltage being applied between the second and third electrodes.

8. The bipolar cutting blade according to claim 1, wherein the first electrode is a longitudinal length of 8–20 mm.

* * * * *